US006613324B1

(12) United States Patent
Blombäck et al.

(10) Patent No.: US 6,613,324 B1
(45) Date of Patent: *Sep. 2, 2003

(54) ADHESIVE FOR THE GLUING OF BIOLOGICAL TISSUES

(75) Inventors: Birger Blombäck, Stockholm (SE); Birgit Hessel, Vällingby (SE); Per Olsson, Stockholm (SE); Lennart Strömberg, Saltsjöbaden (SE); Jesper Swedenborg, Djursholm (SE); Kurt Stocker, Aesch (CH)

(73) Assignee: Bristol-Myers Squibb Company, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/650,027

(22) Filed: May 17, 1996

Related U.S. Application Data

(63) Continuation of application No. 08/301,840, filed on Sep. 7, 1994, now abandoned, which is a continuation of application No. 07/940,941, filed as application No. PCT/CH92/00036 on Feb. 21, 1992, now abandoned.

(30) Foreign Application Priority Data

Feb. 28, 1991 (CH) .............................................. 0606/91

(51) Int. Cl.$^7$ ................................................. A61K 38/48
(52) U.S. Cl. .................... 424/94.64; 424/94.1; 424/542
(58) Field of Search .............................. 424/94.1, 94.64, 424/542

(56) References Cited

U.S. PATENT DOCUMENTS

| 3,657,416 | A | * | 4/1972 | Reid et al. ..................... 424/94 |
| 3,849,252 | A | * | 11/1974 | Percs et al. ................... 195/62 |
| 3,879,369 | A | * | 4/1975 | Nolan ..................... 260/112 R |
| 4,350,625 | A | * | 9/1982 | Abe ....................... 260/112 R |
| 4,377,572 | A | * | 3/1983 | Schwarz et al. ............ 424/101 |
| 4,442,655 | A | * | 4/1984 | Stroetmann .................. 53/428 |
| 4,610,879 | A | * | 9/1986 | Markland, Jr. et al. ........ 424/94 |
| 4,627,879 | A | * | 12/1986 | Rose et al. ................. 106/124 |
| 4,683,142 | A | * | 7/1987 | Zimmermann et al. ........ 427/2 |
| 5,290,552 | A | * | 3/1994 | Sierra et al. ............. 424/94.64 |
| 5,407,671 | A | * | 4/1995 | Heimburger et al. ...... 424/94.1 |

FOREIGN PATENT DOCUMENTS

EP 0534178 3/1993

OTHER PUBLICATIONS

Okada et al., "Fibronectin and Fibrin Gel Structure", J. Biological Chemistry 260 (3) : 1811–20 (1985).*
Shimizu et al., "Ligation of Fibrinogen by Factor XIIIa with Dithiothreitol, Mechanical Properties of Ligated Fibrinogen Gels" Biopolymers 27 (4) : 703–713 (1988).*

* cited by examiner

*Primary Examiner*—Irene Marx
(74) *Attorney, Agent, or Firm*—John M. Kilcoyne

(57) ABSTRACT

Disclosed is an adhesive for gluing of biological tissue, in particular human body tissue. The adhesive contains fibrinogen, a substance capable of supplying calcium ions, blood-coagulating factor XIIIa and, as a fibrinogen-splitting substance, a snake-venom enzyme.

5 Claims, No Drawings

ADHESIVE FOR THE GLUING OF BIOLOGICAL TISSUES

This is a continuation of application Ser. No. 08/301,840, filed Sep. 7, 1994, now abandoned, which in turn is a continuation of application Ser. No. 07/940,941, filed Mar. 29, 1993, also abandoned, which is a 371 of PCT/CH92/00036, filed Feb. 21, 1992.

BACKGROUND OF THE INVENTION

The present invention relates to a fibrinogen-containing adhesive which is intended for the gluing of biological tissues, in particular tissues of the human body.

The physiological wound healing is based on a complex, multistep interaction between proteins, cells and corpuscles of the blood on the one hand, and structure proteins, polysaccharides and cells of the wound on the other hand, finally leading to the filling of the wound with tissue.

Mechanical measures, such as sewing, wedging, nailing and screwing techniques using natural or synthetic, organic or mineral auxiliaries, are often used for the sealing and reconstitution of tissular structures which were broken by surgical interventions or traumatic or pathological influences.

Besides these mechanical procedures, also synthetic chemical gluing systems have been recently tested for the sealing of tissues. Mainly synthetic resin adhesives on the base of polyacrylic acid esters, such as 2-cyanoacrylic acid isobutyl ester (BUCRYLATE™), have been used. However, polyacrylic adhesives give a stiff gluing area which does not fit the plasticity and elasticity of soft tissues and organs, and which causes inflammations due to mechanical irritation. Today, the application of such synthetic resin adhesives is therefore limited to the field of odontology and some special orthopaedic surgical indications.

In order to overcome the mentioned disadvantages of synthetic resin adhesives, it has been tried to use proteins participating in the physiological wound healing as wound-sealing agents. Thus, a commercial product (TISSUCOL$^R$ kit, Immuno AG, Vienna, Austria) has the following composition: A) so-called cryoprecipitate of human blood, a mixture of plasminogen-containing fibrinogen, fibronectin and coagulation factor XIII present as an inactive proenzyme, B) bovine thrombin, C) aprotinin solution and D) calcium chloride solution. Components A and B are lyophilizates which are dissolved in water before use, under dosed addition of components C and D, respectively. The viscous solution A/C, containing 75 to 115 mg of clottable protein per ml, and the solution B/D, containing 4 to 500 units of thrombin according to its application, are then applied on the wound surface either simultaneously or successively, and allowed to polymerize. The thrombin contained in the system catalyzes the splitting of fibrinopeptides (A and B) from fibrinogen and the formation of fibrin monomers as well as the activation of the fibrin-stabilizing factor XIII. Depending on the applied dose of thrombin, an adhesive gluing area sealing the wound defect is formed within few seconds to some minutes, area which is fibrinolytically decomposed and dissolved more or less rapidly according to the aprotinin concentration added.

The bovine thrombin present in gluing systems is an unstable, heat-sensitive enzyme, in which viruses and prions cannot be inactivated or weakened either by physical or chemical measures without destruction of its enzymatic activity, and which, therefore, may be the carrier of bovine spongiform encephalitis (BSE) and of viruses pathogenic to mammals. Furthermore, bovine thrombin is a potent antigen, which can trigger off anaphylactic reactions in the human organism. Although human thrombin is not antigenic, it involves the risk of a transmission of hepatitis and HIV, since it cannot be freed from those viruses either by heat treatment or by chemical measures due to its sensitivity. In the blood, there is finally an inhibitor of thrombin, the so-called antithrombin III, which can neutralize the thrombin of the adhesive. Since this thrombin-inhibiting effect of antithrombin III is potentiated by the anticoagulant heparin, a thrombin-containing adhesive cannot be used, or only under application of high thrombin concentrations, in those patients who undergo a heparin treatment. However, the higher the thrombin concentration in the adhesive, the higher the risk of anaphylactic and thrombo-embolic reactions. In circulating blood, thrombin migrating from the gluing site triggers off an activation of the platelet adhesion, aggregation and release reactions and acts therefore thrombogenic. In order to reduce the risk of anaphylactic and thromboembolic complications to a minimum, it has to be taken great care to keep thrombin away from the tissue which has not to be treated around the wound, during the application of thrombin-containing wound sealants. Thrombin should on no account reach the circulating blood because it can induce thromboses and embolisms due to its multiple activating effects on blood platelets, plasma coagulation factors and endothelium cells. Even in case of careful application, the gluing site constitutes an accumulation of thrombin which can induce intravasal coagulation and against which the organism can develop immunological defence reactions. For these reasons, thrombin-containing fibrin adhesives are only applicable with significant restrictions and are in no way appropriate in case of surgical operations on blood vessels.

Furthermore, due to the short preservability of the dilution, thrombin has to be used in a lyophilized form, what considerably increases the price of the gluing system and complicates its use by an additional dissolution process.

A common disadvantage of all adhesives the clottable protein of which is introduced in the form of a cryoprecipitate lies in their viscous consistency which makes an accurate application impossible. Such viscous or pasty glues are not appropriate in case of microsurgical applications or operations which are performed through the endoscope.

SUMMARY OF THE INVENTION

It has now been tried to overcome the disadvantages of thrombin-containing fibrin adhesives by allowing a fibrinogen-splitting enzyme from a snake venom instead of thrombin as the polymerization inducer to act on a fibrinogen-containing cryoprecipitate solution. Contrary to thrombin which splits fibrinopeptides A and B from fibrinogen and thereby induces an end-to-end and side-by-side polymerization of fibrin, these snake venom enzymes specifically catalyze the exclusive splitting of fibrinopeptide A, which leads to formation of a fragile fibrin which is unsuitable for sealing purposes.

It has now surprisingly been found that the splitting of fibrinopeptide A induced by the snake venom enzyme batroxobin in the presence of calcium ions, in a solution of purified human fibrinogen, leads to the formation of a co-polymerizate with remarkable biophysical properties if activated factor XIII (factor XIIIa) is added to the mixture. The use of purified human fibrinogen, purified human fibronectin and purified human activated factor XIII allows manufacture of lyophilizates of mixtures, which, after reconstitution with water, yield components of a gluing system that have various viscosities and that can be easily and accurately applied.

The present invention relates to an adhesive for the gluing of tissues of the human body which contains (a) fibrinogen, (b) a fibrinogen-splitting enzyme, (c) a calcium ion-providing substance and (d) blood coagulation factor XIII, and which comprises the blood coagulation factor XIII in an activated form (factor XIIIa) and a fibrinogen-splitting snake venom enzyme as the fibrinogen-splitting enzyme.

DETAILED DESCRIPTION OF THE INVENTION

Fibrinogen-splitting snake venom enzymes can be obtained from venoms of the snake family Viperidae. Up to now, 27 fibrinogen-splitting enzymes from venoms of the snake family Viperidae have been isolated and characterized (H. Pirkle and K. Stocker, Thrombin-like enzymes from snake venoms: An inventory. Thromb. Haemostas. 65, 444–450, 1991). Two of these enzymes, ancrod and batroxobin, are used in human medicine as antithrombotic drugs for therapeutic defibrinogenation. They are highly stable in solution, are not inhibited by antithrombin III even in the presence of heparin, are well tolerated by the human organism as very weak antigens, and specifically act on fibrinogen exclusively. Other clotting factors or thrombocyte functions are neither activated nor inhibited by these two enzymes. Thromboembolic side effects are practically excluded. Moreover, as these enzymes derive from reptile species, there is no risk of contamination by viruses or prions pathogenic to mammals.

The adhesive of the present invention can thus be applied not only in the usual indications for fibrin glues, but also in endoscopic operations, e.g. in the articular field and, in particular, in surgical operations in the vascular field.

The sealing capacity of the adhesive of the present invention can be considerably increased by the addition of fibronectin to the gluing mixture.

Furthermore, it has been found that the tensile strength of tissue sealings can be significantly increased if a reduction agent is added to the gluing mixture. Adequate reduction agents are preferably thiol compounds such as cysteine, dithiothreitol, dithioerythrite, glutathion, thioredoxin or similar compounds. The action of these thiol compounds may be due to the stabilization of the active form of factor XIII, which is reduced, and may also be due to exchange reactions between the disulfides of the components of the glue. Dithiothreitol in concentrations of 0.1–1 mM per liter of total adhesive can for example be used.

Before its addition to the gluing mixture, the coagulation factor XIII is activated by means of thrombin, trypsin or thrombocytin, a snake venom enzyme. The activation can be performed as follows: 10 ml of a solution of 500 units of factor XIII in buffered (pH 7.4) 0.05 molar sodium chloride solution are incubated with 100 units of thrombin or 20 units of thrombocytin. The enzymes used for the activation of factor XIII are preferably insolubilized by fixation to an insoluble carrier, e.g., agurose such as SEPHAROSE ™ 4B (Pharmacia, Sweden). After termination of the activation, the insolubilized enzymes can be easily separated from activated factor XIII by centrifugation or filtration.

The snake venom enzymes, being well preservable in solution, have not to be lyophilized, what simplifies the use of the adhesive and reduces its cost price. The fibrinogen-splitting snake venom enzymes can be dissolved in aqueous electrolyte solutions, e.g. in, sodium chloride or calcium chloride solutions. Since the weakly antigenic snake venom enzymes are not inhibited by anti-thrombin also in the presence of heparin, they can even be used at very low doses in patients undergoing a heparin treatment, whereby the risk of anaphylactic reactions is practically excluded. Finally, since snake venom enzymes neither produce the intrinsic or extrinsic prothrombin activation, nor induce adhesion, aggregation and release reactions in blood platelets, the risk of thromboembolic complications is excluded when using the adhesive of the present invention.

Venom gland secretions of solenoglyphous snakes (i.e. those with movable tubular venom fangs) which belong to the family of the viperids (Viperidae), in particular to the pit vipers (Crotalinae), are suitable as raw material for obtaining fibrinogen-splitting snake venom enzymes. Venom of Bothrops atrox, or Bothrops moojeni and Calloselasma (Agkistrodon) rhodostoma, which contain respectively, batroxobin and ancrod, two fibrinogen-splitting enzymes already used in human medicine, are obtained, is particularly appropriate (Stocker, K., Defibrinogenation with thrombin-like snake venom enzymes, in Fibrinolytics and Antifibrinolytics, Markwardt, F., Ed., Springer-Verlag,. Berlin, 1978, 451).

The human proteins fibrinogen and factor XIII used in the adhesive of the present invention are obtained from blood of controlled donors and treated for virus inactivation by chemical and physical processes known as such.

The adhesive of the present invention, in a ready-for-use form, may for example contain 2 to 40 mg of fibrinogen per ml, 0.5 to 10 mg of fibronectin per ml, 0.4 to 2 units of activated factor XIII per ml, 5 to 20 mmoles of calcium chloride per L, 0.1 mmole of sodium chloride per L, 0.05 mmole of buffer ions per L, e.g. Tris-hydroxymethyl-aminomethane (TRIS), and 1 to 100 KIU of aprotinin per ml. Immediately before the application of such mixtures on the tissue to be sealed, the polymerization and gelation of fibrinogen are induced by the addition of an aqueous batroxobin solution. The batroxobin concentration of the solution is adjusted so that the ready-for-use total adhesive contains 5–100 units of batroxobin. With batroxobin quantities of 10 to 50 units per ml of glue mixture gelation times of 10 to 30 seconds are obtained.

The adhesive of the present invention may for example be composed of three individual components in vials to be mixed when needed. Vial 1 contains 20 mg of fibrinogen, 1 mg of fibronectin, 1 unit (KIU) of aprotinin and 1 unit of activated factor XIII in a lyophilized form. Vial 2 contains 1 ml of 0.02 molar calcium chloride solution which serves as the solvent for the contents of vial 1. Vial 3 contains 0.2 ml of an aqueous solution composed of 50 units of batroxobin and 4 µg of dithiothreitol per ml. When using the adhesive, the contents of vial 1 is dissolved in the contents of vial 2. The solution is sucked in a sterile syringe for injections. The solution from vial 3 is sucked in a second syringe for injections. The contents of both syringes are simultaneously applied on the tissue surfaces to be sealed and the latters are assembled under adequate strength.

The properties of the adhesive mixtures of the present invention can be examined on the one hand by chemical and physico-chemical tests of the produced fibrin and on the other hand by measurements of mechanical parameters, such as rigidity, tensile strength and adhesivity of the glue, on various tissues.

Chemical methods for investigating the properties of the glue comprise the determination of the protein mass by amino acid analysis and the degree of reticulation by electrophoretic procedures. Turbidometric measurements and determination of permeability according to Blomback et al. (Biochim. Biophys. Acta 997, 96–110, 1989) allow one to define the porosity and the mean thickness of the fibrin fibers in polymerizates of various adhesive mixtures.

The following new method has been developed for the measurement of the mechanical properties of adhesive mixtures: a circular disk of a selected biological tissue is mounted on one end of a metal cylinder. This end of the cylinder is covered with a metal net of well-defined mesh size to prevent the applied sample of tissue from sliping into the cylinder. The other end of the cylinder is hermetically closed by means of a dense metal plate. A second circular disk of the same biological tissue is mounted in the same way on a second metal cylinder. The adhesive to be tested is now applied on the free-prepared surface of one of the tissue disks and the two latters, mounted on their metal cylinders, are then firmly squeezed against one another. After the achieved polymerization of fibrinogen, both cylinders are put under vacuum, whereby the two samples of tissue are sucked with a known strength against the metal nets covering the ends of the cylinders. Afterwards, a tensile strength at constant velocity is applied on the two metal cylinders and the tensile motion is digitally and graphically recorded with a load cell bound to the system. These graphs record the mechanical properties of the connection established between the biological tissue and the adhesive. To determine the mechanical properties of the adhesive itself, the same test principle is applied, the samples of tissue being however replaced by circular disks of polymerized adhesive.

EXAMPLE 1

An adhesive combination composed of three individual components was manufactured as described thereafter: Component I: 2 g of plasminogen-free human fibrinogen, 0.1 g of human fibronectin, 100 units of factor XIIIa and 100 kallikrein inhibitor units (KIU) of aprotinin were dissolved in 100 ml of an aqueous sterile pyrogen-free buffer solution which contained 0.05 mole per L of Tris-hydroxymethylamino-methane, 0.1 mole per L of sodium chloride and 1 mmole per L of ethylenediaminetetraacetic acid and which presented a pH of 7.4. The solution was sterile filtered through a membrane bacterium filter having a pore size of 0.2 $\mu$, filled under sterile conditions in portions of 1.0 each into 10 ml-vials and lyophilized under sterile conditions. The vials were finally welded. Component II: An aqueous 0.02 molar calcium chloride solution was prepared as the solvent for the lyophilized component I. The solution was filtered fiber-free through a membrane filter, filled into vials with 1 ml each and sterilized for 30 minutes in the autoclave at 120° C. Component III: To activate the calcium ion-containing protein solution obtained by dissolving component I in component II, two batroxobin solutions (IIIa and IIIb) were used with two batroxobin concentrations catalyzing the polymerization of fibrinogen at various velocities. To achieve a slow polymerization, component IIIa was composed of 0.2 ml of a sterile aqueous solution containing 10 units of batroxobin and 4 $\mu$g of dithiothreitol per ml, whereas to achieve a quick polymerization component IIIb contained 0.2 ml of a solution with 50 units of batroxobin and 4 $\mu$g of dithiothreitol per ml. The batroxobin/dithiothreitol solutions IIIa and IIIb were sterilized by sterile filtration and filled under aseptic conditions into vials with 0.2 ml each.

When using the adhesive, component I (lyophilizate) was dissolved in component II (solvent) and component IIIa (slow) or component IIIb (fast) was added to the solution. The slow and fast polymerizing adhesives contained per ml 0.0167 g of fibrinogen, 0.0008 g of fibronectin, 0.833 unit of factor XIIIa, 0.833 KIU of aprotinin, 0.0018 g of $CaCl_2$, 8.333 or 33.333 units of batroxobin, respectively, and 0.66 $\mu$g of dithiothreitol.

EXAMPLE 2

The effect of thrombin and batroxobin on fibrinogen was investigated in the presence or absence of factor XIIIa, respectively.

A solution of factor XIII-containing fibrinogen (1.5 mg/ml in TNE buffer containing 0.05 mole of TRIS, 0.1 mole of NaCl and 1 mmole of EDTA per L) was incubated for 15 hours with thrombin or batroxobin, respectively, in the presence of calcium chloride (20 mmoles per L of reaction mixture). The resulting clot was investigated by turbidity and viscosity measurements. The porosity, $\mu$, i.e. the ratio between the fiber mass and the fiber length and diameter, was calculated. In those experiments where coagulation was triggered off with batroxobin, activated factor XIII (FXIIIa) was added to the reaction mixture. The results of the turbidity and viscosity measurements, expressed by the calculated clot porosity ($\mu$), are summarized in Table I.

TABLE I

| Sample | Thrombin units/ml | Batroxobin units/ml | FXIIIa units/ml (added) | $\mu$ Dalton/cm $\times 10^{-12}$ |
|---|---|---|---|---|
| Fbg + Ba | 0 | 0.9 | 0 | 10.0 |
| Fbg + Ba + FXIIIa | 0 | 0.9 | 0.4 | 3.0 |
| Fbg + Ba + FXIIIa | 0 | 0.9 | 0.4 | 3.0 |
| Fbg + Thr | 1 | 0 | 0 | 4.5 |

Fbg = fibrinogen, Ba = batroxobin, Thr = thrombin, fibrinogen contained 0.4 units of FXIII per ml.

The test results gathered in Table I show that the porosity ($\mu$=ratio between fiber mass and fiber length and diameter) of the gels obtained with batroxobin is lower than that of the gels obtained with thrombin, and that the addition of factor XIIIa can considerably reduce the porosity of the gels obtained with batroxobin, the gels being thereby compressed.

EXAMPLE 3

Gluing of Endothelial Surfaces—Influence of Fibrinogen, Fibronectin and Factor XIIIa on the Maximal Tensile Strength Endothelium samples were prepared from pig aorta. Disks of 1 $cm^2$ diameter were cut from the aorta wall. 100 $\mu$l of adhesive activated with batroxobin (Table II) were pipetted on the endothelial surface of a disk, a second aorta disk being then immediately applied on the adhesive layer so that its endothelial surface was turned towards the glue. The so prepared aorta-adhesive-aorta sandwich was kept for one hour at room temperature. Afterwards, the tensile strength ($N/cm^2$) of the gluing site was measured. The specific composition of the adhesive samples relating to fibrinogen, fibronectin, FXIIIa and activating enzyme is indicated in Table II. In all cases (but the control experiment), calcium chloride in a final concentration of 20 mmoles per L and dithiothreitol in a concentration of 0.5 mmole per L were added to the adhesive. In the control experiment, aorta disks were assembled without adhesive. While investigating the gluing capacity (N/cm²), it was demonstrated that fibrinogen, fibronectin and FXIIIa represent important components of the adhesive polymerized with batroxobin and that the endothelium gluing capacity of this mixture is at least as good as that of the adhesive activated with thrombin.

TABLE II

| | Composition of the adhesive | | | | | |
|---|---|---|---|---|---|---|
| Experiment | Fbg mg/ml | FN mg/ml | FXIIIa units/ ml | Ba units/ ml | Thr units/ ml | Max. tensile strength (N/cm²) |
| 1 | 20 | 2 | 1.6 | 5.4 | 0 | 8.8 |
| 2 | 20 | 0 | 1.6 | 5.4 | 0 | <2.0 |
| 3 | 20 | 2 | 0 | 5.4 | 0 | <2.0 |
| 4 | 20 | 2 | 1.6 | 0 | 4 | 3.6 |
| Control | 0 | 0 | 0 | 0 | 0 | <2.0 |

Fbg = fibrinogen, FN = fibronectin, Ba = batroxobin, Thr = thrombin

EXAMPLE 4

Gluing of Skin—Influence of the Variation of the Fibrinogen and Dithiothreitol Concentration on the Maximal Tensile Strength Pig skin was used to perform these experiments. Pieces of skin of 1 mm thickness were taken from anaesthetized pigs by means of a dermatome and disks were cut thereof. The disks were glued together as described in Example 3, whereby adhesive mixtures activated with batroxobin having various fibrinogen and fibronectin concentrations, with and without dithiothreitol (DTT, final concentration 0.5 mM), respectively, were investigated. In the experiments mentioned in Table III, the clotting time of the activated adhesive amounted to 30 to 40 seconds. The solidity of the gluing, expressed as the maximal tensile strength (N/cm²), was investigated.

TABLE III

| Experiment | Fbg mg/ml | DTT mM | FN mg/ml | FXIIIa units/ ml | Ba units/ ml | Max. tensile strength (N/cm²) |
|---|---|---|---|---|---|---|
| 1 | 20 | 0 | 2 | 1.6 | 22 | >9.0 |
| 2 | 20 | 0 | 2 | 1.6 | 22 | >9.0 |
| 3 | 20 | 0.5 | 2 | 1.6 | 22 | >9.0 |
| 4 | 20 | 0.5 | 2 | 1.6 | 22 | >9.0 |
| 5 | 10 | 0 | 1 | 1.6 | 22 | 5.0 |
| 6 | 10 | 0 | 1 | 1.6 | 22 | 5.0 |
| 7 | 10 | 0.5 | 1 | 1.6 | 22 | >9.0 |
| 8 | 10 | 0.5 | 1 | 1.6 | 22 | >9.0 |

Fbg = fibrinogen, DTT = dithiothreitol, FN = fibronectin, Ba = batroxobin

What is claimed is:

1. A method for gluing tissue comprising:
   (a) contacting a tissue with an adhesive composition comprising:
      (i) 2 to 40 mg/mL fibrinogen;
      (ii) 5 to 100 units/mL batroxobin;
      (iii) 0.5 to 10 mg/mL fibronectin;
      (iv) reducing agent;
      (v) 5 to 20 mmoles/L calcium chloride; and
      (vi) 0.4 to 2 units/mL activated blood coagulation factor XIII;
   (b) permitting said batroxobin to split fibrinopeptide A, from said fibrinogen, thereby gluing said tissue.

2. The method of claim 1 wherein the adhesive composition further comprises a compound selected from the group consisting of aprotinin, antiplasmin and 2-tosyl-amino-4-(4'-amidinophenyl)-butyric acid anilide.

3. The method of claim 1 wherein said reducing agent is selected from the group consisting of cysteine, dithiothreitol, dithioerythrite, glutathione and thioredoxin.

4. The method of claim 1 wherein said adhesive composition further comprises a buffered aqueous electrolyte solution.

5. The method of claim 1 wherein said tissue is human tissue.

* * * * *